(12) United States Patent
Rossi (10) Patent No.: US 7,754,860 B2
(45) Date of Patent: Jul. 13, 2010

(54) METHOD FOR PURIFYING FSH

(75) Inventor: Mara Rossi, Rome (IT)

(73) Assignee: Ares Trading S.A., Aubonne (CH)

( * ) Notice: Subject to any disclaimer, the term of this patent is extended or adjusted under 35 U.S.C. 154(b) by 636 days.

(21) Appl. No.: 10/581,172

(22) PCT Filed: Dec. 16, 2004

(86) PCT No.: PCT/EP2004/014347

§ 371 (c)(1),
(2), (4) Date: Feb. 6, 2007

(87) PCT Pub. No.: WO2005/063811

PCT Pub. Date: Jul. 14, 2005

(65) Prior Publication Data

US 2007/0129295 A1      Jun. 7, 2007

(30) Foreign Application Priority Data

Dec. 22, 2003   (EP) .................................. 03104925

(51) Int. Cl.
C07K 1/14     (2006.01)
C07K 1/16     (2006.01)
C07K 1/18     (2006.01)
C07K 1/22     (2006.01)
C07K 1/20     (2006.01)
C07K 1/34     (2006.01)
C07K 1/36     (2006.01)
C07K 14/59    (2006.01)

(52) U.S. Cl. ........................ 530/412; 530/395; 530/397; 530/398; 530/413; 530/414; 530/416; 530/417

(58) Field of Classification Search ....................... None
See application file for complete search history.

(56) References Cited

U.S. PATENT DOCUMENTS

| 6,162,905 A | 12/2000 | Rapaport et al. |
| 2003/0186893 A1* | 10/2003 | Paradisi et al. ................ 514/16 |
| 2008/0070832 A1 | 3/2008 | Valax et al. |

FOREIGN PATENT DOCUMENTS

| EP | 0 475 779 A1 | 3/1992 |
| EP | 1 106 623 A1 | 6/2001 |
| WO | WO 88/10270 A1 | 12/1988 |
| WO | WO 00/63248 A3 | 10/2000 |

OTHER PUBLICATIONS

Tikhomirov et al., Journal of chromatography, 1978: 167: 197-203.*
Gooding et al., Journal of Chromatography, 1986; 359: 331-337.*
Chiba, K. et al. "Isolation and partial characterization of LH, FSH, and TSH from canine pituitary gland" *Endocrine Journal*, Apr. 1997, pp. 205-218, vol. 44, No. 2.

* cited by examiner

Primary Examiner—Bridget E Bunner
Assistant Examiner—Christina Borgeest
(74) Attorney, Agent, or Firm—Saliwanchik, Lloyd & Saliwanchik (57) ABSTRACT

The invention provides a method for purifying recombinant FSH.

23 Claims, 6 Drawing Sheets

Figure 1    Flow Chart of the purification process of r-hFSH

Figure 2    Preparative chromatographic profile of the Q Sepharose FF step

Figure 3: Preparative chromatographic profile of the IMAC step

Unbound　　　　　Elution　Strip

Figure 4    Preparative chromatographic profile of the DEAE step

Unbound          Strip

Figure 5 Preparative chromatographic profile of the PHENYL step

Unbound  Wash  Elution  Strip

Figure 6 Preparative chromatographic profile of the RPC step

METHOD FOR PURIFYING FSH

CROSS-REFERENCE TO RELATED APPLICATION

This application is the U.S. national stage application of International Patent Application No. PCT/EP2004/014347, filed Dec. 16, 2004, the disclosure of which is hereby incorporated by reference in its entirety, including all figures, tables and amino acid or nucleic acid sequences.

FIELD OF INVENTION

The invention relates to the field of protein purification, particularly the purification of follicle stimulating hormone (FSH).

BACKGROUND OF THE INVENTION

Follicle-stimulating hormone (FSH) is an injectable protein falling into the class of gonadotrophins. FSH is used in the treatment of infertility and reproductive disorders in both female and male patients.

In nature, FSH is produced by the pituitary gland. For pharmaceutical use, FSH may be produced recombinantly (rFSH), or it may be isolated from the urine of postmenopausal females (uFSH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day) for a period of from about 6 to about 12 days.

FSH is also used to induce spermatogenesis in men suffering from oligospermia. A regimen using 150 IU FSH 3 times weekly in combination with 2'500 IU hCG twice weekly has been successful in achieving an improvement in sperm count in men suffering from hypogonadotrophic hypogonadism [Burgues et al.; *Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism; Hum. Reprod.;* 1997, 12, 980-6].

Because of the importance of FSH in the treatment of fertility disorders, the provision of FSH of high purity and high specific activity is desirable. FSH treatment requires repeated injection. Highly purified FSH preparations can be administered subcutaneously, permitting self-administration by the patient, thus greatly increasing patient convenience and compliance.

Lynch et al. [The extraction and purification of human pituitary follicle-stimulating hormone and luteinising hormone; *Acta Endocrinologica,* 1988, 288, 12-19] describe a method for purifying human pituitary FSH. The method involves anion and cation exchange chromatography, and size exclusion chromatography. The method is said to result in pituitary FSH having a specific activity of 4,990 IU (immunoassay)/mg, with 16 IU/mg of LH. Protein content was determined either by dry weight or in solution by absorption at 280 nm (assuming that $A^{280}_{1cm}$ for 1 g/l is equal to 1).

WO 98/20039 (IBSA Institut Biochimique SA) describes a process for the purification of human urinary FSH starting with urinary extracts called human menopausal gonadotrophins (hMG). The process uses ion-exchange chromatography on weakly basic anionic exchange resins of the DEAE type followed by affinity chromatography on resin having an anthraquinone derivative as a ligand. The process is said to yield urinary FSH free from LH and having a specific activity of 6,870 IU (immunoassay)/mg. Protein content was determined by assuming that a water solution of 1 mg/ml of protein has an optical density of 0.62 at 277 nm, in quartz cuvettes with a 1 cm path length.

WO 00/63248 (Instituto Massone SA) describes a process for the purification of gonadotrophins, including FSH, from human urine. The process involves the following steps: ion exchange chromatography with a strong cationic resin of the type sulphopropyl, ion exchange chromatography with a strong anionic resin, and hydrophobic interaction chromatography (HIC). An FSH preparation having a specific activity of 8,400 IU/mg (Steelman-Pohley method: *Assay of the follicle stimulating hormone based on the augmentation with human chorionic gonadotrophin; Endocrinology;* 1953, 53, 604-616) and less than 1 IU LH (rat seminal vesicle weight gain method: Van Hell H, Matthijsen R & G A Overbeek; *Acta Endocrinol,* 1964, 47, 409) biological activity per 75 IU FSH is reportedly obtained. Protein content was performed by the Lowry method [O. H. Lowry et al., *J. Biol. Chem.,* 1951, 193, 265].

U.S. Pat. No. 5,990,288 (Musick et al.) describes a method for purifying FSH from biological samples, such as human pituitary glands or human post-menopausal urine. The process uses dye affinity chromatography. The process is said to result in human pituitary FSH having a specific activity of 7,066 IU (immunoassay)/mg and less than 1 IU (immunoassay)/mg of LH, and a urinary FSH having a specific activity of 6,298 IU (immunoassay)/mg and less than 3 IU (immunoassay)/mg of LH. Protein content was determined by absorption at 280 nm (assuming that $A^{280}_{1cm}$ for 1 g/l is equal to 1).

Chiba et al. [Isolation and partial characterisation of LH, FSH and TSH from canine pituitary gland; *Endocrinol. J.,* 1997, 44, 205-218] describe a technique for purifying canine pituitary gonadotrophins, including FSH, using Concanavalin (Con) A affinity chromatography, hydrophobic interaction chromatography (HIC) and immobilized metal ion chromatography with $Cu^{++}$. The resulting FSH is reported to have a specific activity of 2.17 IU/g protein using a radioreceptor assay for FSH for measuring biological activity and the Bio-Rad protein assay kit (BioRad Laboratories CA USA) for determining protein content.

WO 88/10270 (Instituto di Ricerca Cesare Serono SPA) describes a method for purifying human FSH from urine. The process involves immunochromatography with FSH-specific immobilized monoclonal antibodies bound to Sepharose 4B by divinyl sulphone, followed by reverse phase HPLC. The resulting FSH is free of LH and other urinary proteins and has a specific activity of 6,200 IU/mg of lyophilised powder (Steelman-Pohley method). The preparation was the first FSH preparation to be suitable for subcutaneous administration, due to its great purity.

An ongoing need remains for new methods for purifying FSH.

SUMMARY OF THE INVENTION

It is an object of the invention to provide a new method for purifying recombinant FSH or an FSH variant.

In a first aspect, the invention provides a method for purifying recombinant human FSH or an FSH variant, comprising the steps:

(1) ion exchange chromatography;
(2) immobilised metal ion chromatography;
(3) hydrophobic interaction chromatography (HIC).

which may be carried out in any order.

Abbreviations

The following abbreviations are used in the description of the invention:
FSH: follicle stimulating hormone;
rFSH: recombinant FSH;
hFSH: human FSH;
rhFSH: recombinant human FSH
BV: Bed volume
DEAE: diethylaminoethyl
IMAC: immobilised metal ion affinity chromatography
OD: optical density
HIC: Hydrophobic interaction chromatography
HPLC: high performance liquid chromatography
IRMA: immunoradiometric assay
KD or kD: kiloDalton
HOP: host cell protein, proteins arising from the host cell used for expression of FSH
IPO: In process controls
RP-HPLC: reverse phase high performance liquid chromatography
Q FF: anion exchange on Q sepharose FF

DETAILED DESCRIPTION OF THE INVENTION

The invention provides a method for purifying recombinant human FSH or an FSH variant, comprising the steps:
(1) ion exchange chromatography;
(2) immobilised metal ion chromatography;
(3) hydrophobic interaction chromatography (HIC).

which may be carried out in any order.

The purification method of the invention allows one to obtain a purified FSH of a purity comparable to known FSH products, such as Gonal-F (Serono) and Metrodin-HP (Serono). The starting material for the purification is recombinant FSH.

Preferred Embodiments of the Invention

The purification method of the invention involves a step of ion exchange chromatography. In a preferred embodiment, the step of ion exchange chromatography is carried out with a strong anion exchange resin, particularly preferably a quaternary ammonium resin, such as Q Sepharose FF (Amersham Biosciences), or a resin having similar characteristics, as follows:

| | |
|---|---|
| Type of ion exchanger: | Strong anion |
| Total capacity (mmol/ml): | 0.18-0.25 |
| Exclusion limit (globular proteins): | $4 \times 10^6$ |
| Bead form: | Spherical, diameter 45-165 μm |
| Bead structure: | Cross-linked agarose, 6% |
| Operational pH stability: | 2-12 |
| Cleaning pH stability: | 1-14 |
| Linear flow rate at 25° C. 1 bar 15 cm bed height, XK 50/30 column: | 400-700 cm/h |

In the step of ion-exchange chromatography, elution is preferably carried out using a buffer having a mildly alkaline pH (e.g. at or about 7.2 to at or about 9.0, or at or about 8.0 to at or about 9.0, most preferably at or about 8.5). Suitable buffers include, for example borate buffer, triethanolamine/iminodiacetic acid. Most preferred is borate buffer, at a pH of at or about 8.5. The concentration of the eluting buffer species is preferably within the range of at or about 10 to at or about 100 mM, more preferably at or about 25 to at or about 75 mM, most preferably at or about 50 mM.

Prior to the step of ion exchange chromatography, it may be desirable to carry out a step of ultrafiltration, in order to concentrate the crude FSH. The ultrafiltration (or diafiltration) is preferably carried out using a membrane having a cut-off of at or about 3-10 kD, most preferably at or about 5 kD.

The method of the invention also involves a step of immobilised metal ion chromatography. In a preferred embodiment, the step of immobilised metal ion chromatography is carried out using a resin having tridentate chelate groups, such as, for example, iminodiacetic acid (IDA), and a divalent metal ion, $M^{2+}$, such as $Cu^{2+}$, $Zn^{2+}$, $Ni^{2+}$, $Ca^{2+}$, $Mg^{2+}$ and $Co^{2+}$, preferably $Cu^{++}$. The metal ion-chelating group is attached to a suitable solid support, such as, for example, Sepharose. A particularly preferred resin is Chelating Sepharose FF (Amersham Biosciences), or other resins having similar characteristics, as follows:

| | |
|---|---|
| Composition: | highly cross-linked 6% agarose |
| Particle size: | 45-165 μm |
| Ligand: | iminodiacetic acid groups on spacer |
| Coupling chemistry: | Epoxy |
| Metal ion capacity: | 30-37 μmol $Cu^{2+}$/ml |
| pH stability (operational): | 3-13 |
| pH stability (short term): | 2-14 |
| Pressure/flow spec: | base matrix 200-400 cm/h, 1 bar (100 kPa), XK 50/60 column, bed height 25 cm |

Elution in the step of immobilised metal ion chromatography should be carried out using a buffer of imidazole, phosphate or acetate, particularly preferably acetate, such as ammonium acetate. The pH of the eluent should preferably be at or about 7.5 to at or about 10, more preferably at or about 8.0 to at or about 9.5, particularly preferably at or about 9. The concentration of the buffering species in the eluent should preferably be at or about 0.1 to at or about 2 M, more preferably at or about 0.5 M to at or about 1 M, most preferably at or about 0.75 M.

The method also involves a step of hydrophobic interaction chromatography. In a preferred embodiment, the hydrophobic interaction chromatography is carried out with a resin such as Phenyl Sepharose FF HS (Amersham Biosciences), or a resin having similar characteristics, as follows:

| Matrix: | 6% highly cross-linked spherical agarose |
|---|---|
| Mean particle size: | 90 μm |
| Hydrophobic ligand: | Phenyl |
| Ligand density: | 40 |
| pH stability (short term): | 2-14 |
| pH stability (long term and working range) | 3-13 |

Elution in the step of hydrophobic interaction chromatography is preferably carried out using a buffer having a mildly alkaline pH (e.g. at or about 7.2 to at or about 9, more preferably at or about 7.5 to at or about 8.5, most preferably at or about 8.25). A particularly preferred eluent is Ammonium acetate (50 mM)/Ammonium sulphate (0.25 M), preferably at a pH of at or about 8.25.

After the step of hydrophobic interaction chromatography, it is also possible to carry out a step of reverse phase chromatography (RPC). The RPC is preferably carried out using a resin such as SOURCE 30 RPC (Amersham Biosciences). Elution is preferably carried out using a buffer such as ammonium acetate, preferably at mildly alkaline pH, for example at or about pH 7-8.5, more preferably at or about 7.5 or 7.6. The buffer solution preferably contains at or about 5-25% (volume/volume), preferably at or about 10-20%, of a water miscible organic solvent, preferably a $C_1$ to $C_3$ alcohol, most preferably 2-propanol (iso-propanol).

The steps of ion exchange chromatography, immobilised metal ion chromatography, and hydrophobic interaction chromatography (HIC) may be carried out in any order, although it is preferred to carry out the step of ion exchange chromatography first. The remaining steps of immobilised metal ion chromatography, and hydrophobic interaction chromatography (HIC) may be carried out in any order, although it is preferred to follow the order shown below:

(1) Ion exchange chromatography, (2) Immobilised metal ion chromatography, and (3) hydrophobic interaction chromatography (HIC).

In a further preferred embodiment, between step (2) and step (3) a further step of ion exchange chromatography is carried out (2a), particularly preferably with a weak anion exchange resin, such as for example an exchange resin bearing diaminoethyl groups, particularly DEAE Sepharose FF. In a particularly preferred embodiment, the steps are carried out in the order shown below:

(1) Ion exchange chromatography, (2) Immobilised metal ion chromatography, (2a) second step of ion exchange chromatography, and (3) hydrophobic interaction chromatography (HIC).

In a particularly preferred embodiment, the method of the invention comprises the steps characterised as follows:
(1) ion exchange chromatography (preferably with a strong anion exchange resin, such as Q Sepharose FF);
(2) immobilised metal ion chromatography (preferably with Chelating Sepharose FF, using $Cu^{++}$ as metal ion);
(2a) ion exchange chromatography (preferably with a weak anion exchange resin, such as DEAE Sepharose FF)
(3) hydrophobic interaction chromatography (HIC) (preferably with Phenyl Sepharose FF HS).

The second step of ion exchange chromatography (2a) is preferably carried out using ammonium acetate buffer as eluent, preferably at a pH of at or about 8.5. Preferably the ammonium acetate buffer is at or about 0.05 to at or about 0.5 M, more preferably at or about 0.11 M.

In a further preferred embodiment, after any of the steps of chromatography (particularly preferably after a step of reverse phase chromatography), the FSH sample is submitted to concentration by ultrafiltration. The ultrafiltration (or diafiltration) is preferably carried out using a membrane having a cut-off of at or about 3-10 kD, most preferably at or about 5 kD.

In a particularly preferred embodiment, the following steps are carried out in the order shown below:

(0) Ultrafiltration (preferably with a membrane having a cut-off of at or about 5 kD), (1) Ion exchange chromatography (preferably with Q Sepharose FF), (2) Immobilised metal ion chromatography (preferably with chelating Sepharose FF and $Cu^{++}$), (2a) second step of ion exchange chromatography (preferably DEAE Sepharose FF), (3) hydrophobic interaction chromatography (HIC) (preferably with Phenyl Sepharose FF HS), (4) reverse phase chromatography (RPC) (preferably with Source 30 RPC), and (5) ultrafiltration (preferably with a membrane having a cutoff of 5 kD).

It may be desirable to subject the FSH sample to a step of nanofiltration, in order to ensure that the purified FSH preparation is virus free. Nanofiltration may be done at any stage of the purification process, however, it is particularly preferred to carry out nanofiltration after the $2^{nd}$ step of ion exchange chromatography, or after reverse phase chromatography or after hydrophobic interaction chromatography. Nanofiltration may be performed more than one time, for example it may be performed twice.

In a particularly preferred embodiment, the method of the invention comprises the following steps:

(0) Ultrafiltration (preferably with a membrane having a cut-off of at or about 5 kD), (1) Ion exchange chromatography (preferably with Q Sepharose FF), (2) Immobilised metal ion chromatography (preferably with chelating Sepharose FF and $Cu^{++}$), (2a) second step of ion exchange chromatography (preferably DEAE Sepharose FF), (3) hydrophobic interaction chromatography (HIC) (preferably with Phenyl Sepharose FF HS), (4) reverse phase chromatography (RPC) (preferably with Source 30 RPC), and (5) ultrafiltration (preferably with a membrane having a cutoff of 5 kD), (6) nanofiltration.

Storage/Lyophilisation

The liquid composition resulting from the purification process as described above and containing purified FSH may be frozen for storage as is, or after purification, the eluate may be subjected to lyophilisation ("freeze-drying") to remove solvent. The resulting liquid or lyophilised product is termed "FSH Bulk".

FSH Formulations

FSH or an FSH variant of the invention or purified according to the method of the invention should be formulated for injection, either intramuscular or subcutaneous, preferably subcutaneous.

The FSH formulation may be freeze-dried, in which case it is dissolved in water for injection just prior to injection. The FSH formulation may also be a liquid formulation, in which case it can be injected directly, without prior dissolution.

The FSH formulation may be single dose or multiple dose. If it is multiple dose, it should preferably contain a bacteriostatic agent, such as, for example, benzyl alcohol, meta-cresol, thymol or phenol, preferably benzyl alcohol or meta-cresol. Single dose formulations may also comprise a bacteriostatic agent.

The FSH of the invention may be formulated with known excipients and stabilizers, for example, sucrose and mannitol. It may also comprise an antioxidant, such as methionine. It may further comprise a surfactant, such as TWEEN (preferably TWEEN 20), or Pluronic (preferably Pluronic F68).

In a particularly preferred multidose formulation, FSH produced by the method of the invention is formulated by dissolving it in water for injection with sucrose, phosphate buffer (pH 7), Pluronic F68, methionine and meta-cresol or benzyl alcohol.

Indications

The FSH of the invention is suitable for use in all treatments where FSH is indicated. It is particularly suited for subcutaneous administration in ovulation induction, controlled ovarian hyperstimulation for assisted reproductive technologies, and in the treatment of oligospermia. It may be used in conjunction with other gonadotrophins, such as LH and hCG. It may also be used with compounds which augment the response to FSH, such as clomiphene citrate, aromatase inhibitors, such as Anastrozole, Letrozole, Fadrozole and YM-511.

Sequences:

```
SEQ ID NO. 1:   human glycoprotein α-subunit;
SEQ ID NO. 2:   hFSH β-subunit
SEQ ID NO. 3:   hFSH β-subunit variant 1
SEQ ID NO. 4:   hFSH β-subunit variant 2
SEQ ID NO. 5:   hFSH β-subunit variant 3
```

Follicle stimulating hormone, or FSH, as used herein refers to human FSH (hFSH) produced as a full-length mature protein. FSH is a dimer composed of the human glycoprotein alpha-subunit and the human FSH beta-subunit. The protein sequence of the human glycoprotein alpha subunit is provided in SEQ ID NO: 1, and the protein sequence of the human FSH beta subunit is given in SEQ ID NO: 2.

The use of the term "recombinant" refers to preparations of FSH that are produced through the use of recombinant DNA technology (see for example WO 85/01958). One example of a method of expressing FSH using recombinant technology is by transfection of eukaryotic cells with DNA sequences encoding an alpha and beta subunit of FSH, whether provided on one vector or on two vectors with each subunit having a separate promoter, as described in European patent nos. EP 0 211 894 and EP 0 487 512. The DNA encoding FSH may be a cDNA or it may contain introns. Another example of the use of recombinant technology to produce FSH is by the use of homologous recombination to insert a heterologous regulatory segment in operative connection to endogenous sequences encoding one or both of the subunits of FSH, as described in European patent no. EP 0 505 500 (Applied Research Systems ARS Holding NV). Also contemplated are methods such as those disclosed in WO 99/57263 (Transkaryotic Therapies), wherein one of the subunits is inserted heterologously into a cell, and the other subunit is expressed by activation of genomic sequences by insertion of a heterologous regulatory segment by homologous recombination. The method of the invention may be used to purify FSH expressed using any of these methods.

The expression "recombinant cell" refers to a cell produced by inserting heterologous DNA, including any of the above-mentioned methods of genetic manipulation.

Preferably the FSH is produced recombinantly in Chinese hamster ovary (CHO) cells transfected with a vector or vectors comprising DNA coding for the human glycoprotein alpha-subunit and the beta-subunit of FSH. DNA encoding the alpha and beta-subunits may be present on the same or different vectors.

The expression "FSH variant" is meant to encompass those molecules differing in amino acid sequence, glycosylation pattern or in inter-subunit linkage from human FSH but exhibiting FSH-activity. Examples include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al.; Endocrinology; 1992, 131, 2514-2520; or Klein et al.; Development and characterization of a long-acting recombinant hFSH agonist; Human Reprod. 2003, 18, 50-56]. Also included is single chain CTP-FSH, a single chain molecule, consisting of the following sequences (from N-terminal to C-terminal):

| βFSH | βhCG-CTP(113-145) | αFSH |
|------|-------------------|------| wherein βFSH signifies the β-subunit of FSH, βhCG CTP (113-145) signifies the carboxy terminal peptide of hCG and αFSH signifies the α-subunit of FSH, as described by Klein et al. [*Pharmacokinetics and pharmacodynamics of single-chain recombinant human follicle-stimulating hormone containing the human chorionic gonadotrophin carboxyterminal peptide in the rhesus monkey; Fertility & Sterility;* 2002, 77, 1248-1255]. Other examples of FSH variants include FSH molecules having additional glycosylation sites incorporated in the α- and/or β-subunit, as disclosed in WO 01/58493 (Maxygen), and FSH molecules with intersubunit S—S bonds, as disclosed in WO 98/58957. Further examples of FSH variants include chimeric molecules comprising sequences from FSH and sequences from hCG or LH, such as those described in WO 91/16922 and WO 92/22568.

The FSH variants referred to herein also include the carboxy terminal deletions of the beta subunit that are shorter than the full length mature protein of SEQ ID NO:2. Carboxy terminal deletions of the human beta subunit are provided in SEQ IDS NOS: 3, 4, and 5. It is understood that the carboxy terminal variants of the beta chain form dimers with a known alpha subunit to form an FSH variant heterodimer.

In a preferred embodiment, the FSH is produced recombinantly in CHO cells.

In a preferred embodiment, the purified FSH produced according to the method of the invention is suitable for subcutaneous administration, permitting self-administration by the patient.

The expression "crude recombinant FSH" refers to the cell culture supernatant from recombinant cells expressing FSH, before it has undergone any chromatographic step. The expression encompasses the raw form of the supernatant (as isolated from cells) as well as concentrated and/or filtered and/or ultrafiltered supernatant. The term "biological activity" in relation to FSH activity, refers to the ability of an FSH formulation to elicit biological responses associated with FSH, such as ovarian weight gain in the Steelman-Pohley assay [Assay of the follicle stimulating hormone based on the augmentation with human chorionic gonadotrophin; Endocrinology; 1953, 53, 604-616], or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

LH content in an FSH preparation may be measured, for example, using an LH-specific immunoassay, such as the Delfia hLH Spec (Wallac Oy, Turku, Finland).

The term "specific activity", in reference to FSH, means the biological activity in IU of the preparation in a recognised biological assay for FSH, such as the Steelman Pohley bioassay, divided by the amount of protein, as determined by an assay for total protein content, such as the Lowry assay [O. H. Lowry, N. J. Rosebrough, A. L. Farr and R. J. Randall (1951) *J. Biol. Chem.* 193: 265; Hartree E. E. (1972). *Anal. Biochem.* 48: 422; J. R. Dulley and P. A. Grieve (1975) *Anal. Biochem.* 64: 136], the Bradford assay [Bradford, M. M. (1976) *Anal. Biochem.* 72, 248], or by absorbance at 280 nm. Preferably FSH of the invention has a specific activity of greater than at or about 4000 IU/mg, more preferably greater than at or about 6000 IU/mg, even more preferably greater than at or about 7000 IU/mg, even more preferably greater than at or about 8000 IU/mg wherein biological activity is measured by the Steelman-Pohley bioassay and protein content is measured by the OD at 280 nm.

EXAMPLES

Purification

The following example provides purified r-hFSH starting from concentrated crude r-hFSH produced in 15 and 75 L bioreactors.

Figure 1:
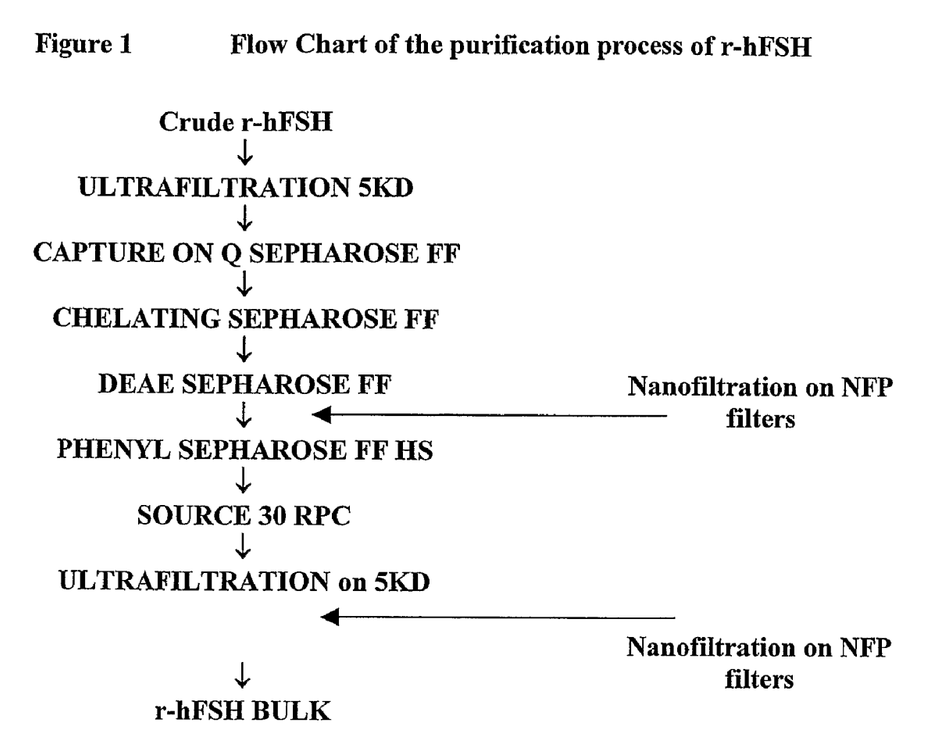
FIG. 1 shows a flow chart showing the purification of rhFSH.

A flow chart of the purification process described in details in the next sections is presented in FIG. 1. The resulting purified rhFSH is termed "rhFSH bulk".

For all buffers pH and conductivity values were referred to +25° C.; i.e. the determination of conductivity value was performed by using an instrument equipped with temperature probe and the obtained value was automatically compensated for difference of temperature and referred to +25° C.

Regarding conductivity measurements, the correlation temperature coefficient was always set at 2.

Step 0: Diafiltration of the Concentrated Crude rhFSH
Equipment
Ultrafiltration system type Pellicon Mini (Millipore or equivalent)
Ultrafiltration membrane at cut off 5 KD in polyethersulphone type BIOMAX (Millipore or equivalent), 0.1 m²
Peristaltic Pump type Masterflex or equivalent
Materials
Concentrated crude r-hFSH
Starting amount: 200-400 mg FSH determined by DELFIA immunoassay for FSH (from 75 L bioreactor)
Sodium Hydroxide pellets—(Merck)
Purified water (Modulab or equivalent)
Boric Acid
Sodium Tetraborate decahydrate
Sodium Hydroxide (pellets)
Borate buffer (50 mM Sodium Borate pH 8.5±0.1): 3.06 gr of Boric Acid and 10 gr of Sodium Tetraborate di-hydrate were added to 900 mL of purified water under stirring, and made up to 1 L.
Ultrafiltration Procedure
All the operations were performed in refrigerated conditions (3-8° C.).

The concentrated crude r-hFSH (1-1.5 L) was ultrafiltered under the following conditions:
Buffer: 50 mM Sodium Borate pH 8.5±0.1, conductivity 1.9±0.2 mS/cm
Flow of the permeate: 15-25 mL/minute
Inlet pressure: 1.5-2.2 bar
Transmembrane pressure: 1.5-1.8 bar
Where:

Transmembrane pressure (TMP)=(Inlet Pressure+ Outlet Pressure)/2

The rhFSH solution was concentrated up to 1 L volume.
The retentate fraction was diluted with 1 volume of purified water and concentrated again up to 1 L (washing);
The washing step was repeated two more times;
The conductivity of the permeate was checked, and if it was less than 1.5 mS/cm the sample was progressed to the next step, otherwise the washing step was repeated.
Permeate Conductivity<1.5 mS/cm
One volume of retentate fraction was diluted to 2 volumes with equilibration buffer and concentrated again up to the original volume.
The operation was repeated two more times.
The pH and conductivity of the permeate were checked and if the pH and conductivity of the permeate fraction were 8.5±0.1 and 1.9±0.2 mS/cm, respectively, the permeate was progressed to the next step, otherwise the washing step was repeated.

Permeate pH=8.5±0.1

Permeate Conductivity: 1.9±0.2 mS/cm

The retentate fraction was collected and the ultrafilter was washed with three aliquots of equilibration buffer, collecting and pooling washes with the retentate fraction in such a way to have a final collected volume of around 0.6-1.2 L.

Collected Volume: 0.6-1.2 L

This fraction was labelled as:
<<Start Q>>
5×0.5 mL samples were stored at −20° C. for IPC.
The volume of the fraction was measured (it can be stored at +5±3° C. for not more than two days).
The samples were analysed as follows: OD at 280 nm, pH, conductivity and r-hFSH content by Immunoassay (DELFIA), and RP-HPLC.
Step 1: Anion Exchange on Q Sepharose FF
Equipment
Chromatographic column XK 50/20
Peristaltic Pump type Masterflex or equivalent
Cold room
UV monitor (optical path Length 2.5 mm) equipped with two channel recorder (Amersham Biosciences or equivalent)
UV Spectrophotometer (Shimadzu or equivalent)
pH meter (Metrohm or equivalent)
Conductometer (Metrohm or equivalent)
Balance (MettlerToledo or equivalent)
Peristaltic pump type Masterflex or equivalent
Materials
Concentrated crude r-hFSH from ultrafiltration step
Starting amount: 200-400 mg FSH by DELFIA
Sodium Hydroxide pellets—(Merck)
Purified water (Modulab or equivalent)

Boric Acid
Sodium Tetraborate decahydrate
Sodium Hydroxide (pellets)
Sodium Chloride
Glacial Acetic Acid
Buffers Equilibration buffer: 50 mM Sodium Borate pH 8.5±0.1, conductivity 1.9±0.2 mS/cm Elution buffer: 50 mM Sodium Borate, 0.13M NaCl pH 8.5±0.1, conductivity 16±1.5 mS/cm Stripping Solution: 1.5M NaCl
Sanitization solution 1: 0.1 M Acetic Acid
Sanitization solution 2: 0.5 M NaOH
Storage solution: 0.01 M NaOH
Column Packing The column was packed with Q Sepharose Fast Flow resin following the manufacturer instructions. The packed column had the following dimensions:

Diameter: 5 cm

Bed height: 11 cm±10%

Bed volume: 190-240 mL
Purification Procedure
All operation were performed at:
Temperature: 3-8° C.
Linear flow rate: 240-280 cm/hour
Column Sanitization The column was flushed with at least 1 BV of NaOH 0.5M, then rinsed with 3 BV of purified water.

Column Equilibration

The column was flushed through with 6-7 or more BV of equilibration buffer, 50 mM Sodium borate pH 8.5±0.1, conductivity 1.9±0.2 mS/cm.

The pH and conductivity were checked and washing was continued until the parameters of the column's effluent were within the following target values:

pH 8.5±0.1, conductivity 1.9±0.2 mS/cm
Starting Material Preparation

The concentrated and diafiltered r-hFSH obtained from the ultrafiltration step was thawed in the amount indicated in the material section.

The pH and conductivity were checked, and samples were saved for IPC (5×0.5 mL).

Loading

The starting material was loaded on the equilibrated column.

Washing

When sample loading was complete, the column was flushed with 2-3 BV of equilibration buffer. The volume collected was recorded, and samples were saved for IPC 5×0.5 mL, and the fraction was discarded.

Elution

Elution was started with 50 mM Sodium Borate, 0.13M NaCl pH 8.5±0.1, conductivity 16±1.5 mS/cm. r-hFSH started to elute after 0.7-1.0 BV from the start.

Figure 2:
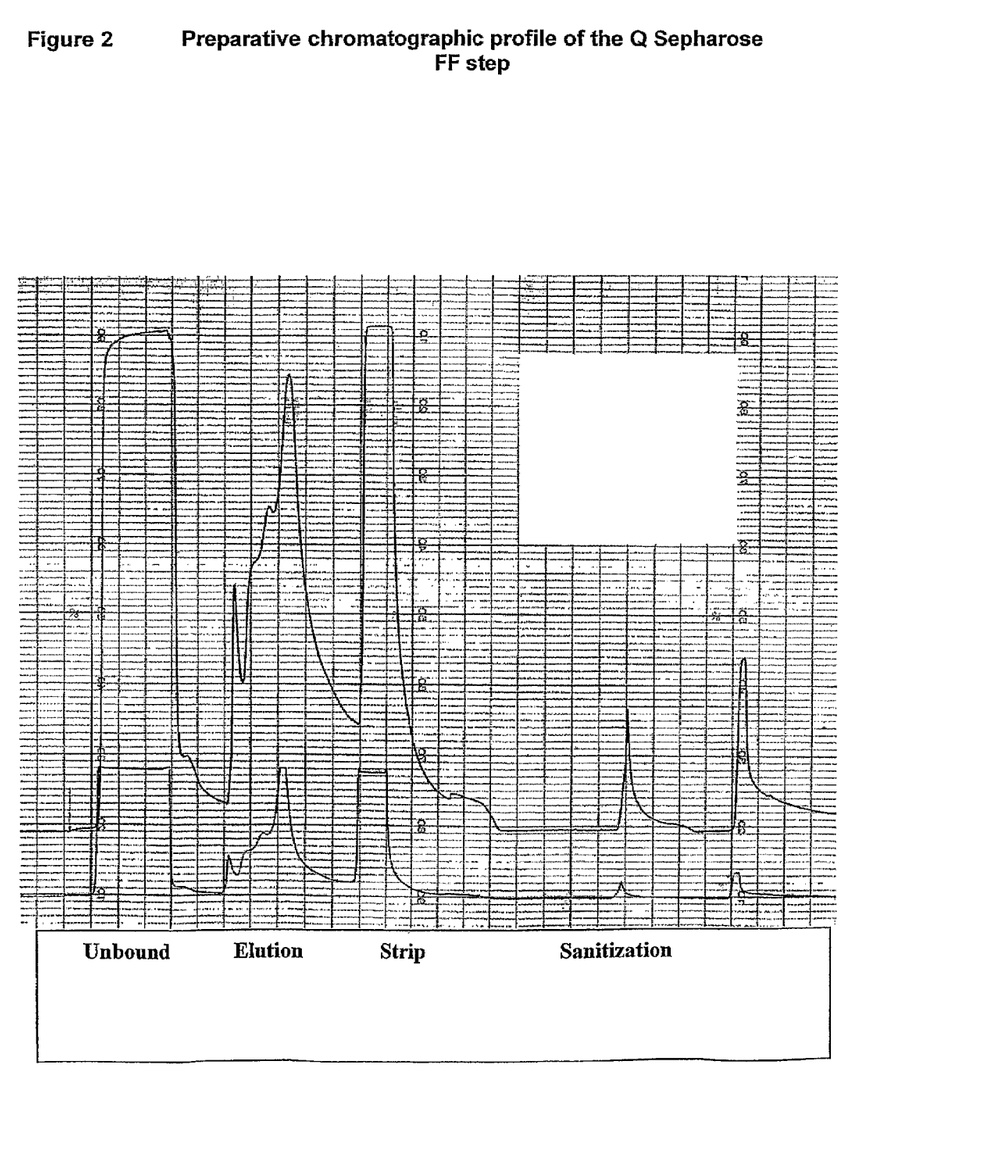
FIG. 2 shows the elution profile for chromatography of crude rhFSH on Q Sepharose FF as detected by OD at 280 nm.

4.5 BV of the elution fraction were collected, showing two peaks, according with the chromatographic profile depicted in FIG. 2.

The volume collected was recorded, and samples for IPC were withheld (5×0.5 mL).

The fraction could be stored at 4° C. for not more than two days.

This fraction contains the semipurified r-hFSH
Step (2): IMAC on Chelating Sepharose FF
Equipment
Chromatographic column C10/40 (Amersham Biosciences)
Peristaltic Pump type miniplus 2 Gylson or equivalent
UV monitor (optical path Length 2.5 mm) equipped with two channel recorder (Amersham Biosciences or equivalent)
Cold room
UV Spectrophotometer (Shimadzu or equivalent)
pH meter (Metrohm or equivalent)
Conductometer (Metrohm or equivalent)
Balance (MettlerToledo or equivalent)
Peristaltic pump type Masterflex or equivalent
Materials
Post Q Sepharose FF r-hFSH
Sodium Hydroxide pellets—(Merck)
Purified water (Modulab or equivalent)
Boric Acid
Sodium Tetraborate decahydrate
Sodium Hydroxide (pellets)
Sodium Chloride
EDTA
Ammonium Acetate
Copper Sulphate
25% Ammonia solution
Buffers
Metal charge solution: 0.2M Copper sulphate
Acidified water: 1 mL of glacial acetic acid was added to 1 L of purified water under stirring.
Equilibration buffer: 50 mM Sodium Borate pH 8.25±0.1, 0.5M NaCl
Elution: 0.75 M Ammonium Acetate pH 9.0±0.1, conductivity ±0.5 mS/cm
Regeneration solution: 0.5M NaCl, 50 mM EDTA
Sanitizing solution: 0.5M NaOH
Storage solution: 0.01M NaOH
Column Packing The column was packed with Chelating Sepharose Fast Flow resin following the manufacturers' instructions. The packed column had the following dimensions:

Diameter: 10 mm

Bed height: 22±10%

Bed volume: 16-20 mL
Purification Procedure
All operations were performed at:
Temperature: 5±3° C.
Linear flow rate: 240-300 cm/hour
Column Sanitization The column was flushed with at least 1 BV of NaOH 0.5M then rinsed with 3 BV of purified water.

Column Charge

The column was flushed with 5-6 BV of acidified water until the pH was <4.5 (with pH-indicator). The column was then flushed with 3 BV of 0.2M Copper sulphate and again 4-5 BV of acidified water until the Absorbance value (280 nm) reached the baseline.

Column Equilibration

The column was flushed through with 6 or more BV of equilibration buffer, 50 mM Sodium phosphate pH 8.25±0.1, 0.5M NaCl, conductivity 50±5 mS/cm.

The pH and conductivity were checked and washing was continued if the parameters of the column's effluent were outside of the target values:

pH 8.25±0.1, conductivity 50±5 mS/cm
Starting Material Preparation r-hFSH obtained from the Q Sepharose FF step was adjusted to pH to 8.25±0.1 by adding 35% ortho-phosphoric acid, and conductivity to 50±5 mS/cm by adding NaCl.

Samples were withdrawn for IPC (5×0.5 mL).

Loading

The starting material was loaded on the column equilibrated as above.

Washing

When sample loading was completed, the column was flushed with 5-10 BV of equilibration buffer 50 mM Sodium phosphate pH 8.25±0.1, 0.5M NaCl, conductivity 50±5 mS/cm.

Samples were withdrawn (5×0.5 ml) for IPC and the fraction was discarded.

Elution

Elution was started with 0.075M ammonium Acetate pH 9.0±0.1, conductivity 7.2±0.5 mS/cm.

r-hFSH started to elute as a main peak after 0.5 BV from the start.

5-7 BV were collected of the main peak starting when the on line OD steeply increased, approximately after the first 0.5 BV discarded.

Samples were withdrawn for (IPC 5×0.5 mL) and the fraction was stored at 3°-8° C. for not more than two days.

Figure 3:
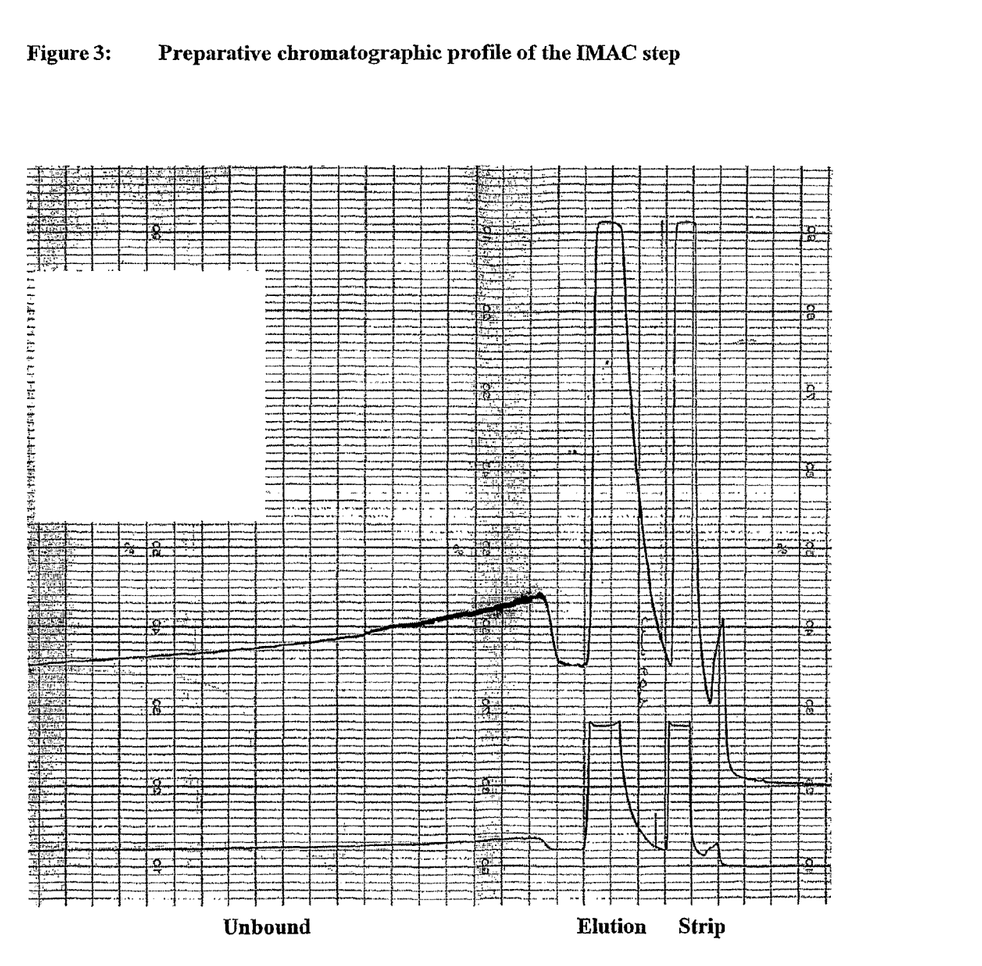
FIG. 3 shows the elution profile for IMAC chromatography of partially purified rhFSH as detected by OD at 280 nm.

The elution profile for the IMAC is shown in FIG. 3.

This fraction contained the semipurified r-hFSH

Step (2a): Anion Exchange on DEAE Sepharose FF

Equipment

Chromatographic column Vantage L 22/40

Peristaltic Pump type miniplus 2 Gylson or equivalent

Cold room

UV monitor (optical path Length 2.5 mm) equipped with two channel recorder (Amersham Biosciences or equivalent)

UV Spectrophotometer (Shimadzu or equivalent)

pH meter (Metrohm or equivalent)

Conductometer (Metrohm or equivalent)

Balance (MettlerToledo or equivalent)

Peristaltic pump type Masterflex or equivalent

Materials

Post IMAC r-hFSH

Sodium Hydroxide pellets—(Merck)

Purified water (Modulab or equivalent)

Sodium Hydroxide (pellets)

Sodium Chloride

Ammonium Acetate

25% Ammonia solution

Buffers

Equilibration buffer: 0.11 M Ammonium acetate pH 8.5±0.1, conductivity ±0.5 mS/cm Regeneration solution: 1.5M NaCl Sanitizing solution: 0.5M NaOH Storage solution: 0.01M NaOH Column Packing The column was packed with DEAE Sepharose Fast Flow resin following the manufacturers' instructions. The packed column had the following dimensions:

Diameter: 22 mm

Bed height: 16-17 cm

Bed volume: 65-70 mL

Purification Procedure

All operation were performed at:

Temperature: 5±3° C.

Linear flow rate: 240-300 cm/hour

Column Sanitization

The column was flushed with at least 1 BV of NaOH 0.5M, and then rinsed with 3 BV of purified water.

Column Equilibration

The column was flushed with 6 or more BV of equilibration buffer, 0.11 M Ammonium Acetate pH 8.5±0.1, conductivity 10.2±0.5 mS/cm.

The pH and conductivity were checked and washing was continued if the parameters of the column's effluent were out of target values:

pH 8.5±0.1, conductivity 10.5±0.5 mS/cm

Starting Material Preparation r-hFSH obtained from the IMAC step was brought to pH 8.5±0.1 by adding glacial acetic acid, and conductivity to 10.5±0.5 mS/cm by adding purified water (one volume of water at least is necessary to adjust the conductivity to the target value.

Samples were withdrawn for IPC (5×0.5 mL).

Loading

The starting material was loaded on the column equilibrated as above.

Washing

When sample loading was complete, the column was flushed with 3-6 BV of equilibration buffer 0.11 M Ammonium Acetate pH 8.5±0.1, conductivity 10.2±0.5 mS/cm.

Figure 4:
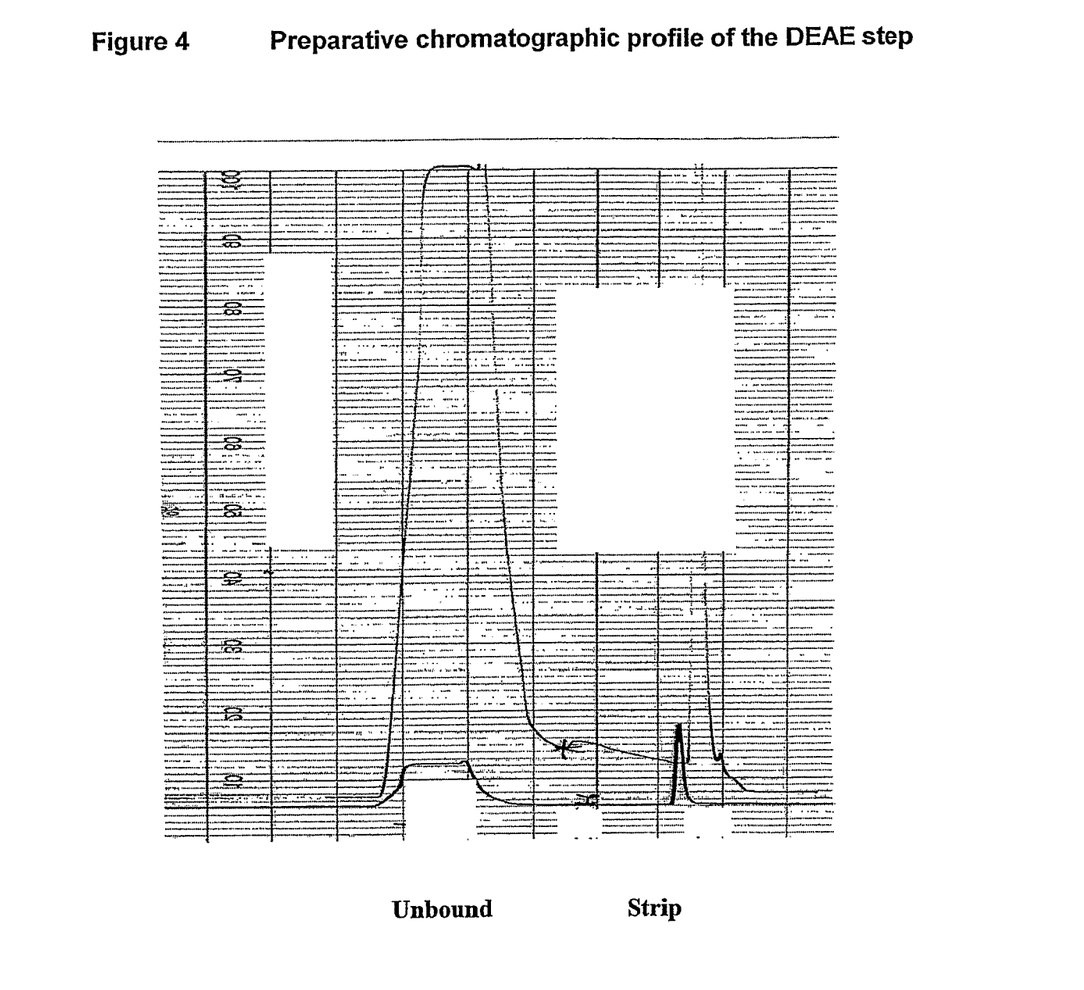
FIG. 4 shows the elution profile for DEAE Sepharose chromatography of partially purified rhFSH as detected by OD at 280 nm.

Samples were withdrawn for IPC (5×0.5 mL) and the fraction was stored at +5±3° C. for not more than two days. The elution profile for DEAE Sepharose FF chromatography is shown in FIG. 4.

Step (3): Hydrophobic Interaction on Phenyl Sepharose FF HS

Equipment

Chromatographic column XK 26/30

Peristaltic Pump type miniplus 2 Gylson or equivalent

UV monitor (optical path Length 2.5 mm) equipped with two channel recorder (Amersham Biosciences or equivalent)

Cold room

UV Spectrophotometer (Shimadzu or equivalent)

pH meter (Metrohm or equivalent)

Conductometer (Metrohm or equivalent)

Balance (MettlerToledo or equivalent)

Peristaltic pump type Masterflex or equivalent

Materials

Post DEAE r-hFSH

Sodium Hydroxide pellets—(Merck)

Purified water (Modulab or equivalent)

Sodium Hydroxide (pellets)

Sodium Chloride

Ammonium Acetate

Ammonium Sulphate

25% Ammonia solution

Buffers

Equilibration buffer: 50 mM Ammonium acetate, 1M Ammonium Sulphate pH 8.25±0.1, conductivity 142±8 mS/cm Wash buffer: 50 mM Ammonium acetate, 0.9M Ammonium Sulphate pH 8.25±0.1, conductivity 130±5 mS/cm Elution buffer: 50 mM Ammonium acetate, 0.25M Ammonium Sulphate pH 8.25±0.1, conductivity 50±3 mS/cm Strip solution: purified water Sanitizing solution: 0.5M NaOH Storage solution: 0.01M NaOH Column Packing The column was packed with Phenyl Sepharose Fast Flow HS resin following the manufacturers' instructions. The packed column had the following dimensions:

Diameter: 34 mm

Bed height: 14-15 mm

Bed volume: 125-135 mL

Purification Procedure

All operations were performed at:

Temperature: 5±3° C.

Linear flow rate: 240-300 cm/hour

Column Sanitization

The column was flushed with at least 1 BV of NaOH 0.5M, then rinsed with 3-5 BV of purified water.

Column Equilibration

The column was flushed through with 5-6 or more BV of equilibration buffer: 50 mM Ammonium acetate, 1M Ammonium Sulphate pH 8.25±0.1, conductivity 140±8 mS/cm The pH and conductivity were checked and washing was continued until the parameters of the column's effluent were within target values:

pH 8.25±0.1, conductivity 140±8 mS/cm

Starting Material Preparation r-hFSH obtained from the DEAE step was added with 1 M Ammonium Sulphate and brought to pH 8.25±0.1 by adding 25% Ammonia solution.

Samples were withdrawn for IPC (5×0.5 mL) and the fraction was loaded on the Phenyl column.

Loading

The starting material was loaded on the column equilibrated as above.

Washing Post Load

When sample loading was complete, the column was flushed with 3-6 BV of equilibration buffer: 50 mM Ammonium acetate, 1M Ammonium Sulphate pH 8.25±0.1, conductivity 140±5 mS/cm Samples were withdrawn for IPC (5×0.5 mL) and the fraction was discarded.

Washing

When sample loading was complete, the column was flushed with 3-6 BV of wash buffer 50 mM Ammonium acetate, 0.9M Ammonium Sulphate pH 8.25±0.1, conductivity 130±5 mS/cm Samples were withdrawn for IPC (5×0.5 mL) and the fraction was discarded.

Elution

Figure 5:
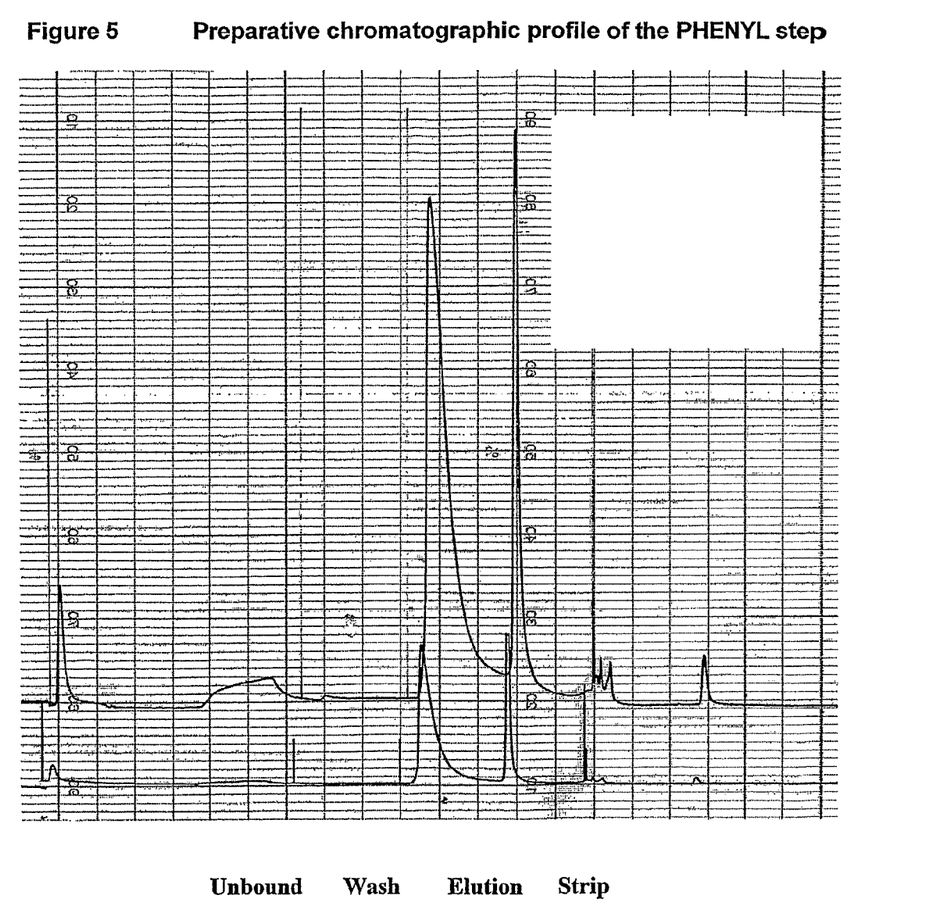
FIG. 5 shows the elution profile for Phenyl Sepharose chromatography of partially purified rhFSH as detected by OD at 280 nm.

Elution was started with elution buffer.

r-hFSH started to elute as a main peak after 0.5-0.8 BV from the start. 3-4 BV of the main peak were collected starting when the Absorbance value (280 nm) increased, according to the chromatographic profile depicted in FIG. 5.

Samples were withdrawn for IPC (5×0.5 mL) and stored at +5±3° C. for not more than one days.

Step (4): Reverse Phase on Source 30 RPC

Equipment

Chromatographic column: Vantage L 22/40

UV monitor (optical path Length 2.5 mm) equipped with two channel recorder (Amersham Biosciences or equivalent)

Peristaltic pump (Minipulse 2 Gillson or equivalent)

UV Spectrophotometer (Shimadzu or equivalent)

pH meter (Metrohm or equivalent)

Conductometer (Metrohm or equivalent)

Balance (Mettler Toledo or equivalent)

Materials r-hFSH intermediate post HIC

SOURCE 30 RPC resin (Amersham Biosciences)

Ammonium Acetate—Merck

Glacial Acetic Acid—Merck

Sodium hydroxide pellets—Merck—

50% NaOH solution—J. T. Baker

25% Ammonia solution—Merck 2-propanol—Merck

Sodium Hydroxide pellets—Merck

Buffers

Base buffer: 50 mM Ammonium Acetate pH 7.6±0.2, conductivity 6.5±0.5 mS

Equilibration buffer: 50 mM Ammonium Acetate pH 7.6±0.2, containing 13% of 2-propanol (V/V)

Elution buffer: 50 mM Ammonium Acetate 7.6±0.2, containing 20% of 2-propanol (V/V)

Regeneration solution: 50 mM Ammonium Acetate 7.6±0.2, containing 35% of 2-propanol (V/V)

Sanitizing solution: 0.5M NaOH

Storage solution: 0.01M NaOH

Column Packing

The column was packed with SOURCE 30RPC resin following the manufacturers' instructions. The packed column had the following dimensions:

Diameter: 22 mm

Bed height: 13-14 cm

Bed volume: 49.4-53.2 mL

Purification Procedure

Starting Material Preparation

Post HIC intermediate was loaded onto the column in 13% (V/V) of 2-propanol.

All operation were performed at:

Temperature: room temperature (+20±5° C.)

Linear flow rate: 300-450 cm/hour

Column Sanitization

The column was flushed with at least 1 BV of NaOH 0.5 M and rinsed with 6 BV of purified water.

Column Equilibration

The column was flushed with 7-10 or more BV of equilibration buffer, 50 mM Ammonium Acetate pH 7.6±0.2, containing 13% of 2-propanol (V/V).

Loading

The starting material r-hFSH post HIC prepared as above was loaded on the column.

Post Load Wash

When sample loading was complete, the column was flushed with 7-10 BV of equilibration buffer.

Samples were withdrawn for IPC (5×0.5 mL), and the fraction was discarded.

Elution

Figure 6:
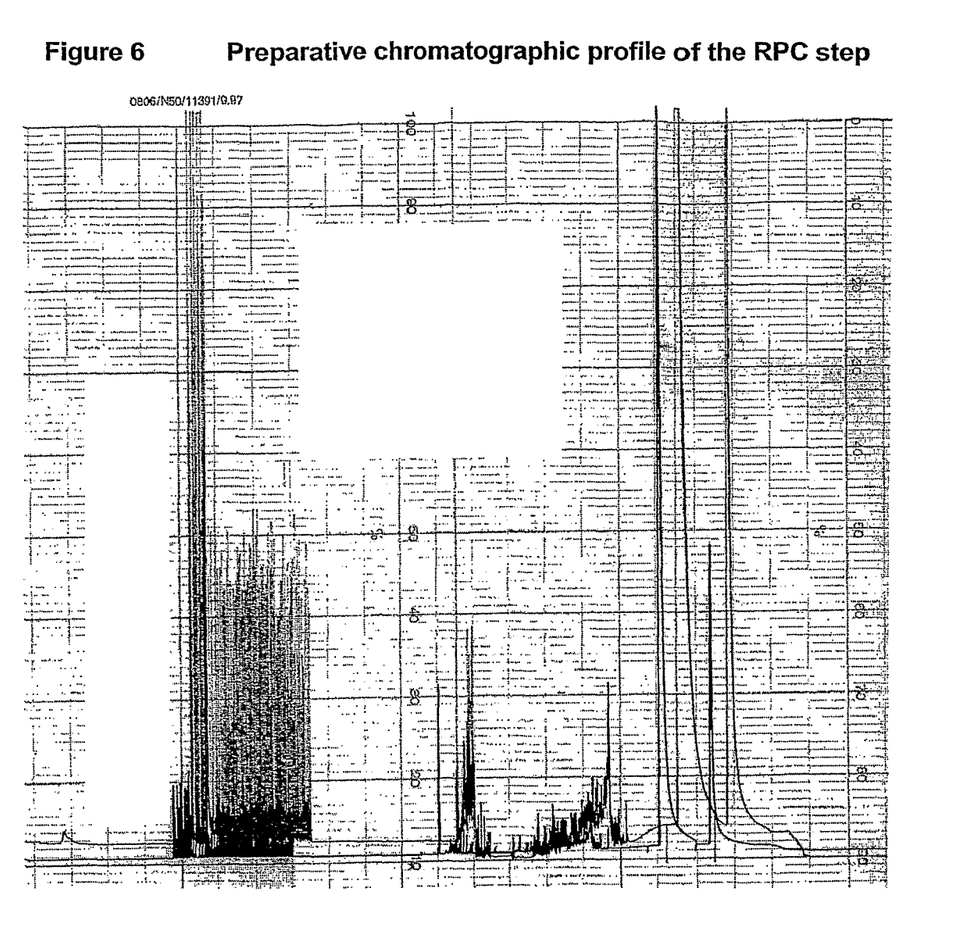
FIG. 6 shows the elution profile for the RPC step using a Source 30 RPC column.

Elution was started with elution buffer.

r-hFSH started to elute as a main peak after 0.5-0.8 BV from the start. 5-7 BV of the main peak were collected starting when the Absorbance value (280 nm) increased, according to the chromatographic profile depicted on FIG. 6. After collection was complete the solution was diluted 1:2 with purified water to reduce the percentage of 2-propanol in contact with r-hFSH.

Samples were withdrawn for IPC (5×0.5 mL) and stored at +5±3° C. for not more than one days.

This fraction contained purified r-hFSH.

Column Regeneration

After elution was complete the column was flushed with at least 3 BV of regeneration buffer.

Samples were withdrawn for IPC (5×0.5 mL), and the fraction was discarded.

Sanitization

The column was flushed with at least 1-2 BV of water followed by 3 BV NaOH 0.5M, the flow was stopped for 1 hour, and the column was then rinsed with 6 BV of purified water.

Storage

The column was flushed with at least 3 BV of storage solution, 0.01M NaOH and stored until the next cycle.

Step (5) Bulk Ultrafiltration

Equipment

1 Vivaflow 200 PES, RC or Hydrosart cut off 5KD (Sartorius)
Peristaltic pump (type Masterflex L/S)
UV Spectrophotometer (type Shimadzu or equivalent)
pH meter (type Mettler Toledo or equivalent)
Conductivity meter (type Metrohm or equivalent)

Materials r-hFSH—HIC Eluate
Sodium hydroxide pellets—Merck (NaOH).
Purified water by Modulab or equivalent
Nitrogen (operative pressure: 3 bars)—UPP grade.

Buffers

Diafiltration solution: the ultrafiltration of the r-hFSH was carried out using purified water.
Sanitizing solution: 0.5 M NaOH
Storage solution: 0.05 M NaOH Procedure All operations were performed in a cool room (+5±3° C.).

Ultrafiltration

The r-hFSH—HIC eluate solution was recirculated in the Vivaflow system and concentrated to a volume lower than 20 mL.

The retentate fraction was diluted with 4 volumes of purified water and concentrated up to <20 mL.

The washing step was repeated as described, 5-7 more times.

The pH and conductivity of the permeate were 7.1±0.2 and 6.2±0.5 mS/cm respectively. If outside these values, the washing step was repeated.

Permeate pH=7.1±0.2

Permeate Conductivity=6.2±0.5 mS/cm

The retentate fraction was collected in a volume suitable to obtain a final concentration of r-hFSH by OD (280 nm) of around 0.5-0.7 mg/mL.

Samples were withdrawn (10×0.5 mL) for analysis. Both samples and bulk were stored at −20° C.

Step (6) Nanofiltration STEP for Virus Removal

Materials and Equipment r-hFSH intermediate solution (post DEAE or ultrafiltered post RPC);
47 mm sized pre-filters type Fluorodine II FTKDJL (Pall) or VVLP 0.1μ(Millipore);
47 mm sized filters type NFP (Millipore) or DV20 (Pall);
Purified water;
pH paper indicators;
Sodium hydroxide;
Nitrogen regulated source;
Complete stainless steel filtration system (Millipore);
Silicons and tygon tube.

Buffers

Sanitizing solution: 0.5 M NaOH

Procedure

All operations were performed at room temperature (+23±3° C.)

Nanofiltration

The system was filled with post DEAE or ultrafiltered post RPC rFSH, pre-filtered on 0.1μ filters. At the beginning of the filtration the Nitrogen was opened until an initial pressure of 0.5 bar and the vent valve located on the disc-holder was opened in order to purge the system.

As soon as the first drop of solution appeared, the vent valve of the disc-holder was closed and the nitrogen pressure was raised to 2.3-2.8 bar.

The nitrogen pressure was maintained at 2.3-2.8 bar and the solution was filtered.

The operative conditions are summarised below:

| Parameter | Range |
|---|---|
| Sample | Post DEAE or ultrafiltred Post RPC rFSH |
| Nitrogen pressure | 2.3-2.7 bar |
| Flow rate (mL/min) | 0.1-0.3 mL/min with Pall filter on the post DEAE |
| | 0.3-0.6 mL/min with Millipore filter on the post DEAE |
| | 0.1-0.2 mL/min with Pall filter on the ultrafiltered post RPC |
| | 1-1.5 mL/min with Millipore filter on the ultrafilterd post RPC |

Biological Activity of Samples

The biological activity of the purified rhFSH was measured using the Steelman-Pohley ovarian weight gain method. Specific activity was calculated using the biological activity divided by the protein content as determined by absorbance at 280 nm (assuming that $\epsilon$=9.95 $M^{-1}$ $cm^{-1}$), and also by using the biological activity divided by the protein content as determined by the Lowry method. Specific activity of the purified rhFSH bulk is shown in Table 1.

TABLE 1

Specific activity of bulk purified rhFSH of the invention

| Analysis | Sample |
|---|---|
| Protein concentration by OD (mg/ml) | 0.64 |
| Specific activity (Biological activity/OD) | 8876 IU/mg |
| Protein concentration by Lowry (mg/ml) | 0.75 |
| Specific activity (Biological activity/Lowry) | 7594 IU/mg |

The invention claimed is:

1. A method for purifying recombinant human follicle stimulating hormone (FSH) or an FSH variant comprising the steps of subjecting FSH to:

(1) ion exchange chromatography at a pH of about 8.5;

(2) immobilised metal ion chromatography at a pH of about 9; and (3) hydrophobic interaction chromatography (HIC) at a pH of about 8.25.

2. The method of claim 1, wherein the ion exchange chromatography is carried out with a strong anion exchange resin.

3. The method of claim 2, wherein the anion exchange resin is a quaternary ammonium chromatography resin.

4. The method of claim 1, wherein the ion exchange chromatography is carried out using borate buffer as eluent.

5. The method of claim 4, wherein the borate buffer is at a pH of at or about 8.5.

6. The method of claim 1, wherein the immobilised metal ion chromatography is carried out with a resin having tridentate chelating groups.

7. The method of claim 6, wherein the chelating groups are iminodiacetic acid.

8. The method of claim 1, wherein the immobilised metal ion chromatography is carried out with a metal ion selected from $Cu^{2+}$, $Zn^{2+}$, $Ni^{2+}$, $Ca^{2+}$, $Mg^{2+}$ and $Co^{2+}$.

9. The method of claim 1, wherein the immobilised metal ion chromatography is carried out with $Cu^{2+}$.

10. The method of claim 1, wherein the immobilised metal ion chromatography is carried out using ammonium acetate as eluent.

11. The method of claim 10, wherein the ammonium acetate buffer has a pH at or about 9.

12. The method of claim 1, wherein the hydrophobic interaction chromatography (HIC) is carried out using chromatography resin comprising phenyl groups.

13. The method of claim 1, wherein the hydrophobic interaction chromatography is carried out using ammonium acetate (50 mM)/ammonium sulphate (0.25 M) as eluent.

14. A method for purifying recombinant human follicle stimulating hormone (FSH) or an FSH variant comprising the steps of subjecting FSH to:
(1) ion exchange chromatography;
(2) immobilised metal ion chromatography;
(2a) ion exchange chromatography; and
(3) hydrophobic interaction chromatography (HIC), wherein a second step of ion exchange chromatography (2a) is carried out after the step of immobilised metal ion chromatography, and before the step of hydrophobic interaction chromatography (HIC).

15. The method of claim 14, wherein the second step of ion exchange chromatography is carried out using a weak anion exchange resin.

16. The method of claim 15, wherein the weak anion exchange resin comprises diethylaminoethyl groups.

17. The method of claim 1, further comprising a step of reverse phase chromatography (4), carried out after the step of hydrophobic interaction chromatography (HIC).

18. The method of claim 17, wherein the reverse phase chromatography is carried out using a solution comprising ammonium acetate (50 mM, pH at or about 7.6) with 20% (v/v) 2-propanol.

19. The method of claim 17, comprising a step of ultrafiltration (5), carried out after the step of reverse phase chromatography.

20. A method for purifying human recombinant follicle stimulating hormone FSH comprising the steps of subjecting FSH to:

(i) ultrafiltration;
(ii) anion exchange chromatography on a resin comprising quaternary ammonium groups with a solution comprising about 50 mM borate, about 013 M NaCl, at a pH of about 8.5 as eluent;
(iii) subjecting the eluate of step (ii) to a step of immobilised metal ion affinity chromatography on a resin comprising tridentate chelate groups, with $Cu^{++}$ as metal ion, with an solution of about 0.75 M ammonium acetate at a pH of about 9 as eluent;
(iv) subjecting the eluate of step (iii) to a step of anion exchange chromatography on a resin comprising diethyldiaminoethyl groups, with a solution comprising about 0.11 M Ammonium acetate, pH of about 8.5 as eluent;
(v) subjecting the eluate of step (iv) to a step of hydrophobic interaction chromatography on a chromatography resin comprising phenyl groups with a solution comprising about 50 mM ammonium acetate, about 0.25 M ammonium sulphate, at a pH of about 8.25 as eluent;
(vi) subjecting the eluate of step (v) to a step of reverse phase chromatography on a reverse phase chromatography resin, with a solution comprising about 50 mM ammonium acetate, pH of about 7.6, and about 20% of 2-propanol (v/v);
(vii) subjecting the eluate of step (vi) to a step of ultrafiltration; and
(viii) subjecting the retentate of step (vii) to a step of nanofiltration.

21. The method of claim 1, comprising a second step of ion exchange chromatography (2a), carried out after the step of immobilised metal ion chromatography, and before the step of hydrophobic interaction chromatography (HIC).

22. The method of claim 21, wherein the second step of ion exchange chromatography is carried out using a weak anion exchange resin.

23. The method of claim 22, wherein the weak anion exchange resin comprises diethylaminoethyl groups.

* * * * *

UNITED STATES PATENT AND TRADEMARK OFFICE
CERTIFICATE OF CORRECTION

PATENT NO.       : 7,754,860 B2                                                    Page 1 of 1
APPLICATION NO.  : 10/581172
DATED            : July 13, 2010
INVENTOR(S)      : Mara Rossi It is certified that error appears in the above-identified patent and that said Letters Patent is hereby corrected as shown below:

Column 3,
Line 40, "HOP: host cell protein" should read --HCP: host cell protein--.
Line 42, "IPO: In process controls" should read --IPC: In process controls--.

Column 8,
Line 20, "50-56]." should read --50-56.--.

Column 15,
Line 53, "than one days" should read --than one day--.

Column 16,
Line 63, "than one days" should read --than one day--.

Column 18,
Line 35, "ultrafilterd" should read --ultrafiltered--.

Column 24,
Line 4, "about 013" should read --about 0.13--.

Signed and Sealed this

Sixteenth Day of November, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 92

```
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 3
<211> LENGTH: 108
<212> TYPE: PRT
<213> ORGANISM: Homo sapiens

<400> SEQUENCE: 3

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu
            100                 105
```

-continued

```
<210> SEQ ID NO 4
<211> LENGTH: 109
<212> TYPE: PRT
<213> ORGANISM: Homo sapiens

<400> SEQUENCE: 4

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met
                100                 105

<210> SEQ ID NO 5
<211> LENGTH: 110
<212> TYPE: PRT
<213> ORGANISM: Homo sapiens

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys
                100                 105                 110
```